United States Patent [19]

Cherkofsky

[11] 4,267,190
[45] May 12, 1981

[54] ANTIINFLAMMATORY 4,5-DIARYL-α,α-BIS(POLYFLUOROMETHYL)-1H-PYRROLE-2-METHANETHIOLS

[75] Inventor: Saul C. Cherkofsky, Wilmington, Del.

[73] Assignee: E. I. Du Pont de Nemours and Company, Wilmington, Del.

[21] Appl. No.: 141,663

[22] Filed: Apr. 18, 1980

[51] Int. Cl.$^3$ .................. A61K 31/40; C07D 207/323; C07D 207/333; C07D 401/04
[52] U.S. Cl. .............................. 424/274; 260/326.47; 260/326.5 S; 260/326.9; 260/326.5 SF; 424/245; 424/263; 546/6; 546/281
[58] Field of Search ......... 260/326.9, 326.47, 326.5 S, 260/326.5 SF; 546/6, 281; 424/245, 263, 274

[56] References Cited

U.S. PATENT DOCUMENTS 3,709,906  1/1973  Yoshida et al. .............. 260/326.5 N

OTHER PUBLICATIONS

Snmuszkovicz et al., J. Med. Chem., vol. 9, pp. 527–536, (1966).
Middleton, J. Org. Chem., vol. 30, p. 1390, (1965).

*Primary Examiner*—Alton D. Rollins

[57] ABSTRACT

4,5-Diaryl-α,α-bis(polyfluoromethyl)-1H-pyrrole-2-methanethiols, such as 4,5-bis(4-fluorophenyl)-α, α-bis(trifluoromethyl)-1H-pyrrole-2-methanethiol, useful in treatment of inflammation.

24 Claims, No Drawings

ANTIINFLAMMATORY 4,5-DIARYL-α,α-BIS(POLYFLUOROMETHYL)-1H-PYRROLE-2-METHANETHIOLS

BACKGROUND OF THE INVENTION

This invention relates to antiinflammatory pyrroles.

J. Szmuszkovicz et al., *J. Med. Chem.*, 9, 527 (1966) describe synthesis and biological activity of a clinically tested antiinflammatory agent of the formula

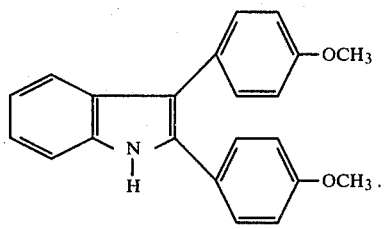

Yoshida et al., U.S. Pat. No. 3,709,906 disclose 5-alkyl-2,3-diphenylpyrrole derivatives which are useful as antiinflammatory agents.

W. J. Middleton, *J. Org. Chem.*, 30, 1390 (1965) includes disclosure of the compound:

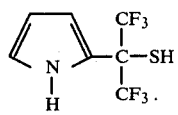

Pharmaceutical use is not disclosed.

There is a continuing need for safe and effective antiinflammatory agents. Inflammation is a disease process characterized by redness, fever, swelling and pain. Arthritis, in its various forms, is the most prevalent, chronic, and severe of the inflammatory diseases. Traumatic injury and infection also involve inflammation, and antiinflammatory drugs are often used in their treatment. The usefulness of most commercial antiinflammatories is limited because of toxicity and adverse sideeffects. Many produce gastric irritation and other effects, such as changes in blood cells and central nervous system. Adreno-cortical steroids produce gastric irritation and suppression of normal adrenal function.

The present invention results from efforts to develop new anti-arthritic compounds with good antiinflammatory activity and minimal side effects that could be more effective in treating arthritis than presently available drugs.

In addition to antiinflammatory properties, some compounds of this invention have demonstrated analgesic activity in a test procedure. This additional property is desirable in treatment of arthritis or related diseases; however, such compounds can be employed solely to alleviate pain.

SUMMARY OF THE INVENTION

This invention relates to compounds of Formula I, pharmaceutical compositions containing them, and methods of use of these compounds to treat arthritis.

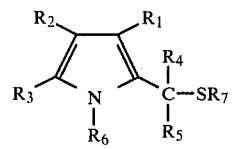

wherein
$R_1$ = H or $C_1$-$C_2$ alkyl;
$R_2$ and $R_3$ independently = 3-pyridyl or

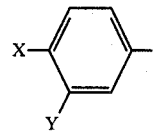

where
$X$ = H, F, Cl, Br, $C_1$-$C_2$ alkyl, $C_1$-$C_2$ alkoxy, di($C_1$-$C_2$ alkyl)amino or $CH_3S(O)_n$— where n = 0, 1 or 2; and
$Y$ = H, F or Cl; with the proviso that when Y is F or Cl, then X is F or Cl;
$R_4$ and $R_5$ independently = $CF_3$, $CF_2H$, $CF_2Cl$, or $CFCl_2$
$R_6$ and $R_7$ independently = H, $C_1$-$C_6$ alkyl, $C_1$-$C_6$ alkanoyl, benzyl or benzyl substituted with up to two atoms selected from the group consisting of F, Cl, Br, $NO_2$, and $CF_3$; or
a pharmaceutically suitable acid addition salt where $R_2$ or $R_3$ is 3-pyridyl or dialkylaminophenyl; or
a pharmaceutically suitable metal salt where $R_7$ is H.

PREFERRED COMPOUNDS

Preferred compounds for utility consideration or ease of synthesis are those in which, independently:
(a) $R_1$ = H or $CH_3$; or
(b) $R_2$ and $R_3$ independently =

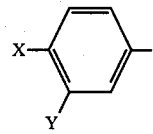

and where X = Cl, F or $CH_3O$ and Y = H; or
(c) $R_4$ and $R_5$ = $CF_3$; or
(d) $R_6$ = H or $CH_3$; or
(e) $R_7$ = H or $CH_3$.
Specifically preferred for the same reasons is:

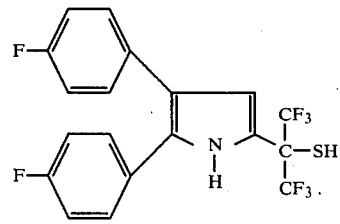

SYNTHESIS

The compounds of this invention can be prepared from 2,3-diarylpyrroles. One method of preparation of 2,3-diarylpyrroles involves reaction of substituted α-aminodesoxybenzoins with acetylene diesters, followed by hydrolysis and decarboxylation according to the procedure used by J. Szmuszkovicz et al., *J. Med. Chem.*, 9, 527 (1966) and by U.S. Pat. No. 3,462,451, the disclosure of which are hereby incorporated by reference, for the synthesis of 2,3-bis(4-methoxyphenyl)pyrrole. (Scheme I).

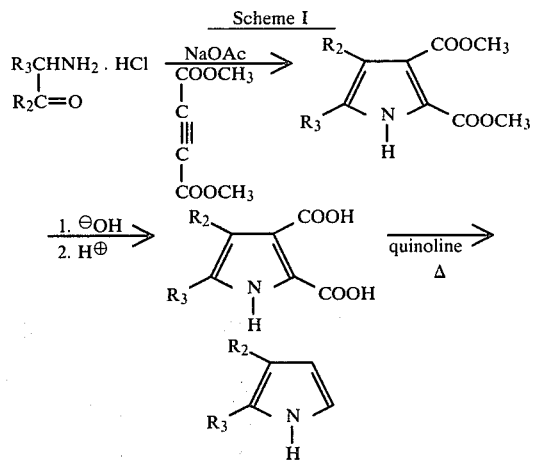

Another method of preparation of 2,3-diarylpyrroles is a modification of the procedure of T. Severin and H. Poehlmann, *Chem. Ber.*, 110, 491 (1977), hereby incorporated by reference, which describes the preparation of monoaryl pyrroles. By using substituted desoxybenzoins, the desired 2,3-diarylpyrroles are formed (Scheme II).

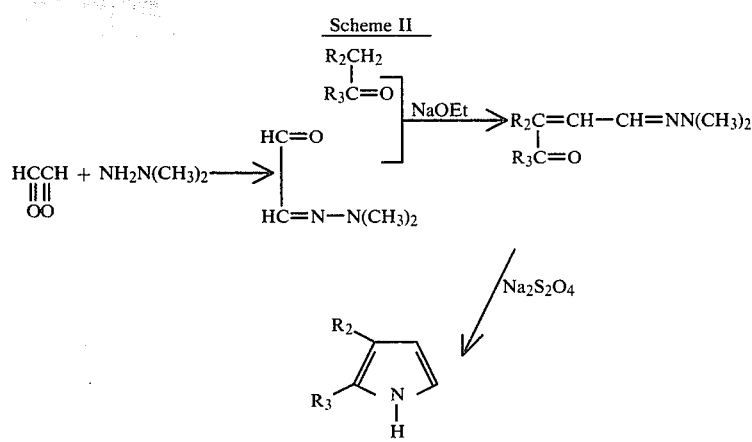

Preparation of 2,3-diaryl-4-alkylpyrroles can be accomplished by several methods. First, 4,5-diarylpyrrole-3-carboxylae esters, prepared, for instance, by the method of A. M. van Leusen et al., *Tet. Letters*, 5337 (1972) can be reduced to the 2,3-diaryl-4-methylpyrroles by lithium aluminum hydride [following the general procedure of R. L. Hinman and S. Theodoropulos, *J. Org. Chem.*, 28, 3052 (1963)], hereby incorporated by reference.

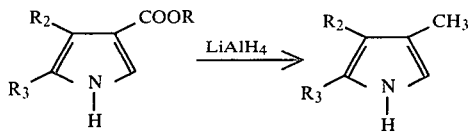

Secondly, 2,3-diaryl-4-alkylpyrroles can be prepared by the general procedure of N. Engel and W. Steglich, *Angew. Chem. Int. Ed. Engl.*, 17 676 (1978), hereby incorporated by reference, from N-allylcarboxamides.

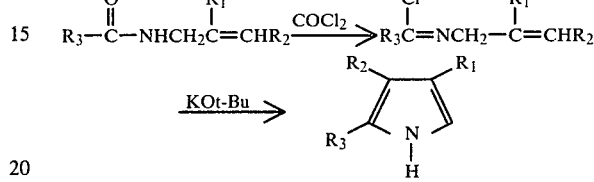

1-Alkyl-2,3-diarylpyrroles can be prepared from the corresponding 2,3-diarylpyrroles by treatment with a strong base, such as sodium hydride, followed by alkylation using an alkyl halide, or, other suitable alkylating reagent, such as methyl iodide.

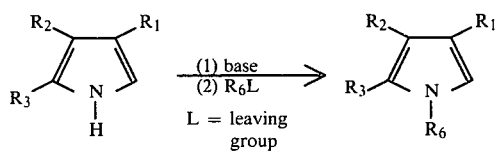

$R_6'$ = alkyl, benzyl or substituted benzyl.

1-Alkanoyl-2,3-diarylpyrroles can be prepared by treatment of the 2,3-diarylpyrrole with acylating agents, such as acetyl chloride or acetic anhydride in the presence or absence of a base

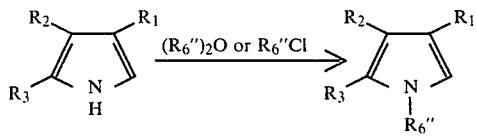

$R_6''$ = alkanoyl.

Introduction of the α,α-bis(polyfluoromethyl)methanethiol group is accomplished by reaction of the 2,3-diarylpyrrole with a fluorinated thioketone, such as hexafluorothioacetone. This reaction can be conducted in a solvent, such as toluene, at

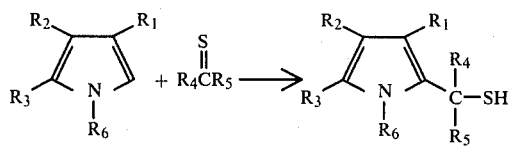

temperatures from 0° to the reflux temperature of the solvent. Acidic catalysts such as AlCl₃, BF₃, p-toluenesulfonic acid, trifluoroacetic acid or the like may be employed, but are not required. Reaction times are usually from less than one hour to 24 hours. The use of hexafluorothioacetone in toluene at ambient temperature without catalyst is preferred.

Compounds of Formula I of this invention with $R_6$ and/or $R_7$ not equal to H can be prepared by alkylation or acylation of the corresponding compounds with $R_6$ and/or $R_7$ equal to H. Alkylation or acylation can occur on either or both of the N and S functionalities, depending on the conditions of the reaction. Often, mixtures of products are obtained. These alkylations or acylation can be conducted in the presence or absence of a base, such as

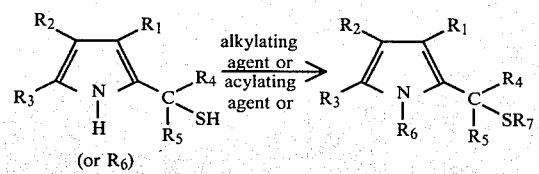

potassium carbonate, pyridine, triethylamine, potassium t-butoxide, sodium hydride or the like. Examples of alkylating and acylating agents are methyl iodide, benzyl chloride, acetic anhydride and acetyl chloride.

Pharmaceutically suitable salts of the compounds of Formula I can be of two types. First, when one or both aryl groups is a dialkylaminophenyl or a 3-pyridyl group, acid addition salts can be prepared by treatment of the free base I with the appropriate acid. Second, pharmaceutically suitable metal salts (forming the salt of the acidic SH) can be prepared by treatment of compounds of the formula I with strong bases such as hydroxides, hydrides, alkoxides, or the like.

In the following examples, all parts are by weight and temperatures are in degrees centigrade unless otherwise specified.

PREPARATION 1

2,3-Diphenylpyrrole (Method A)

A. Dimethyl 4,5-diphenylpyrrole-2,3-dicarboxylate

In a 2 l RB 3-neck flask with mechanical stirrer and condenser was placed 76.7 g (0.31 mole) of desyl amine hydrochloride [Pschorr et al., Chem. Ber., 35, 2740 (1902)], 750 ml methanol, 88 g (0.62 mole) dimethyl acetylenedicarboxylate (freshyl distilled) and 61 g (0.75 mole) anhydrous sodium acetate. The mixture was then heated at reflux for two hours. Then another 44 g (0.31 mole) of dimethyl acetylenedicarboxylate was added, and heating continued another two hours. While the reaction mixture was still at reflux, concentrated hydrochloric acid (∼60 ml, to pH ∼2) was added dropwise. The mixture was heated at reflux another hours, then poured into 2 l water containing 200 ml 10% sodium bicarbonate solution, With stirring, more sodium bicarbonate was added until the solution was neutral. The gummy solid which precipitated was collected and washed with water. Trituration of this gummy material with ∼500 ml of 50% aqueous ethanol gave a tan powdery solid, which was recrystallized from ∼85% aqueous ethanol to give 65.5 g (63%) of white crystals, m.p. 191°-2° [Lit. m.p. 185°-7°; J. B. Hendrickson et al., J. Am. Chem. Soc., 86, 107 (1964)].

B. 4,5-Diphenylpyrrole-2,3-dicarboxylic Acid

To a mixture of 57.5 g (0.172 mole) of dimethyl 4,5-diphenylpyrrole-2,3-dicarboxylate in 350 ml methanol was added a solution of 71 g (1.78 mole) of sodium hydroxide in 350 ml water. The mixture was heated at reflux for two hours, then cooled in an ice bath. The insoluble white crystals were collected and washed with cold methanol to give the bis sodium salt of the product. The still damp solid was dissolved in 1 l cold water and acidified with conc. hydrochloric acid. The precipitated product was collected by filtration, washed with water containing ∼1% hydrochloric acid, then air dried and finally dried in a vacuum oven at 100° to give 50.0 g (95%) of white solid, m.p. 216°-218° (dec., depends on heating rate).

C. 2,3-Diphenylpyrrole (Method A)

A mixture of 20 g (0.065 mole) of 4,5-diphenylpyrrole-2,3-dicarboxylic acid in 80 ml quinoline was heated at reflux in an oil bath (bath ∼230°) until gas evolution stopped (approx. one-half hour). The reaction mixture was cooled and most of the quinoline was removed by distillation (bp 58°@0.2 mm). The partially crystalline residue was chromatographed on 300 g Silic AR CC-7, eluting with toluene to give 12 g (85%) of faintly pink 2,3-diphenylpyrrole which could be further purified by recrystallization from ethanol/water or by sublimitation (∼125°@0.2 mm) to give white solid, m.p. 132°-3°.

Anal. Calcd. for $C_{16}H_{13}N$: C, 87.64; H, 5.98; N, 6.39. Found: C, 87.99; H, 5.86; N, 6.50.

PREPARATION 2

2,3-Diphenylpyrrole (Method B)

A. Glyoxal mono(dimethylhydrazone) was prepared by the procedure of T. Severin and H. Poehlmann, Chem. Ber., 110, 491 (1977) to give 36.1 g (80%) of pale yellow liquid, bp 109° (22 mm); lit. bp 90° (16 mm).

B. 4-Dimethylhydrazono-1,2-diphenyl-2-buten-1-one

To a mixture of 19.6 g (0.1 mole) desoxybenzoin and 10 g (0.1 mole) of glyoxal mono(dimethylhydrazone) in 100 ml ethanol was added dropwise a solution of sodium ethoxide prepared by dissolving 2.3 g (0.1 mole) sodium metal in 100 ml ethanol. The mixture was heated at reflux for one-half hour. TLC (90/10, toluene/ethyl acetate) showed a small amount of starting desoxybenzoin, so 2.0 g (0.02 mole) of additional glyoxal mono(dimethylhydrazone) was added. Heating was continued another two hours. TLC at this time showed no starting material, and two clean close yellow product spots (isomers). The mixture was poured into 1 l ice water and then extracted with methylene chloride. The organic extracts were dried and concentrated on a rotary evaporator to give 28.7 g (100%) of yellow oil. The NMR showed the presence of two major $N(CH_3)_2$ containing materials (product isomers). The crude oil crystallized from isopropanol to give one pure isomer of product, 13.4 g (48%), pale yellow crystals, m.p. 131°-2°.

Anal. Calcd. for $C_{18}H_{18}N_2O$: C, 77.67; H, 6.52; N, 10.06. Found: C, 77.44; H, 6.46; N, 10.17.

C. 2,3-Diphenylpyrrole (Method B)

A mixture of 3.1 g (0.011 mole) of 4-dimethylhydrazono-1,2-diphenyl-2-buten-1-one, 11.2 g (0.064 mole) sodium hydrosulfite in 75 ml ethanol and 37.5 ml water was heated at reflux for three hours. The mixture was cooled and poured into 300 ml ice water. The white crystalline product was collected, washed with water and air dried to give 1.9 g (79%), m.p. 130°–1°, identical to product obtained via the decarboxylation, Method A.

PREPARATION 3

2,3-Diphenyl-4-methylpyrrole

A. Ethyl 4,5-diphenylpyrrole-3-carboxylate was prepared by a procedure similar to that used by A. M. van Leusen et al., *Tet. Letters*, 5337 (1972) for the preparation of the methyl ester. The ethyl ester was obtained as a white solid, m.p. 207°–208.5° (methyl cyclohexane/toluene).

Anal. Calcd. for $C_{19}H_{17}NO_2$: C, 78.33; H, 5.88; N, 4.81. Found: C, 77.92; H, 5.87; C, 77.90; H, 5.88; N, 4.60. N, 4.62.

B. 2,3-Diphenyl-4-methylpyrrole

To a stirred slurry of 0.76 g (20 mmoles) of lithium aluminum hydride in 25 ml THF was added dropwise a solution of 0.58 g (2 mmoles) of ethyl 4,5-diphenylpyrrole-3-carboxylate in 5 ml THF. The mixture was heated at reflux overnight. After cooling, 0.8 ml water, 2.4 ml 15% sodium hydroxide solution and 0.8 ml water were added dropwise. The solids were removed by filtration and the filtrate concentrated by rotary evaporation. The crystalline residue was purified by chromatography on 50 g silicic acid (CC-7) eluting with hexane/toluene (90/10) to give 0.25 g of product, m.p. 163°–164° C.

Anal. Calcd. for $C_{17}H_{15}N$: C, 87.51; H, 6.48; N, 6.00. Found: C, 87.77; H, 6.60; N, 5.89.

PREPARATION 4

2,3-Bis(4-fluorophenyl)-4-methyl-1H-pyrrole

A. 3-(4-Fluorophenyl)-2-methyl-2-propen-1-al

To a solution of 124 g (1 mole) of 4-fluorobenzaldehyde and 8 g (0.143 mole) of potassium hydroxide in 500 ml ethanol at room temperature was added dropwise a solution of 52.2 g (0.9 mole) of propionaldehyde in 100 ml ethanol. After stirring for 0.5 hour, the mixture was acidified with acetic acid and concentrated by rotary evaporation. The residue was partitioned between methylene chloride and water. The aqueous layer was extracted three times with additional methylene chloride. The combined organic layers were dried and concentrated. Distillation through a 12-inch vacuum jacketed column gave 113.5 g (77%) of pale yellow low-melting crystalline product, b.p. 70°–72° C. (0.4–0.7 mm).

Anal. Calcd. for $C_{10}H_9FO$: C, 73.16; H, 5.53. Found: C, 72.89, 72.72; H, 5.66, 5.46.

B. 3-(4-Fluorophenyl)-2-methyl-2-propen-1-ol

To a solution of 113 g (0.69 mole) of 3-(4-fluorophenyl)-2-methyl-2-propen-1-al in 800 ml ethanol at 10° C. was added in portions 13.1 g (0.345 mole) of sodium borohydride. After the addition was complete, the reaction mixture was stirred at room temperature overnight. The mixture was cooled in an ice bath while 350 ml of 1 N hydrochloric acid was added dropwise to give a final pH of ~7. The mixture was diluted with 500 ml water and extracted three times with methylene chloride. The organic extracts were dried and concentrated and the residue distilled to give 56.1 g (49%) of colorless liquid, b.p. 68°–70° C. (0.15 mm).

Anal. Calcd. for $C_{10}H_{11}FO$: C, 72.27; H, 6.67. Found: C, 72.30, 72.38; H, 6.61, 6.62.

C. 1-Chloro-3-(4-fluorophenyl)-2-methyl-2-propene

To a solution of 53.6 g (0.32 mole) of 3-(4-fluorophenyl)-2-methyl-2-propen-1-ol in 100 ml methylene chloride was added dropwise a solution of 57.1 g (0.48 mole) of thionyl chloride in 100 ml methylene chloride. The reaction mixture was stirred at room temperature for 2 hours, then concentrated by rotary evaporation. The product was checked by NMR, then used crude in the reaction with ammonia.

D. 3-(4-Fluorophenyl)-2-methyl-2-propen-1-amine

A quantity of 59.1 g (0.32 mole) of 1-chloro-3-(4-fluorophenyl)-2-methyl-2-propene and 500 ml ethanol was loaded in a pressure vessel. The vessel was cool-evacuated and 100 g of ammonia was added. The mixture was heated at 95° for 3 hours with shaking. The vessel was cooled, vented and the contents rinsed out with ethanol. The mixture was concentrated by rotary evaporation. The residue was diluted with 1.5 l water and acidified with concentrated hydrochloric acid. This mixture was filtered to remove some insoluble solid (undissolved amine hydrochloride). The aqueous filtrate was extracted with ether to remove any non-basic impurities. The aqueous layer was combined with the insoluble solid and made basic with 5% sodium hydroxide solution. This was then extracted with ether and the ether extracts were dried and concentrated. Distillation of the residue gave 22.8 g (43%) of colorless liquid, b.p. 57° C. (0.2 mm).

Anal. Calcd. for $C_{10}H_{12}FN$: C, 72.70; H, 7.32; N, 8.48. Found: C, 72.67, 72.59; H, 7.48, 7.53 N, 8.31.

E. 4-Fluoro-N-[3-(4-fluorophenyl)-2-methyl-2-propenyl]-benzamide

To a vigorously stirred mixture of 19.8 g (0.12 mole) of 3-(4-fluorophenyl)-2-methyl-2-propen-1-amine and 30.2 g (0.36 mole) of sodium bicarbonate in 500 ml water at 5° C. was added dropwise 22.2 g (0.14 mole) of 4-fluorobenzoyl chloride. The mixture was stirred another 3 hours at 5° C. then at room temperature overnight. The white solid which had formed was collected, washed with saturated sodium bicarbonate solution, then with water, then with hexane, then air dried to give 33.4 g (97%) of product, m.p. 107°–109° C.

Anal. Calcd. for $C_{17}H_{15}F_2NO$: C, 71.07; H, 5.26 N, 4.88. Found: C, 70.85; H, 5.48; N, 4.70.

F. 2,3-Bis(4-fluorophenyl)-4-methyl-1H-pyrrole

Using the general procedure of N. Engel and W. Steglich, *Angew. Chem. Int. Ed. Engl.*, 17, 676 (1978), to a slurry at room temperature of 28.7 g (0.1 mole) of 4-fluoro-N-[3-(4-fluorophenyl)-2-methyl-2-propenyl]-benzamide in 100 ml toluene containing 1 ml DMF, stirred under nitrogen, with a dry ice condenser attached, was added dropwise a solution of 39.6 g (28.3 ml, 0.4 mole) of phosgene in 100 ml toluene. The mixture was warmed slightly with a heat gun, then stirred at room temperature overnight. The solution was concentrated by rotary evaporation to give a yellow oil. This was dissolved in 100 ml dry THF (small amount of insoluble solid removed by decanting the solution) and the solution was added dropwise to a cool (15°) solution of 33.5 g (0.3 mole) of potassium t-butoxide in 150 ml DMSO. The dark purple solution was stirred at ~20° C. for 1 hour, then was poured into 1 liter ice water. This was extracted with ether and the ether layers backwashed with water. The ether layer was dried and concentrated and the residue was chromatographed on 900 g of silica gel, eluting with hexane containing 10–40% toluene, to give, after recrystallization from methyl cyclohexane, 10.8 g (40%) of white product, m.p. 126°–7° C.

Anal. Calcd. for $C_{17}H_{13}F_2N$: C, 75.82; H, 4.87; N, 5.20. Found: C, 75.87; H, 4.85; N, 5.13.

PREPARATION 5

2,3-bis(4-fluorophenyl)-1-methyl-1H-pyrrole

To a mixture of 1.5 g (0.038 mole) of 60% sodium hydride dispersion and 100 ml DMSO was added dropwise a solution of 5.1 g (0.02 mole) of 2,3-bis(4-fluorophenyl)-1H-pyrrole in 25 ml DMSO. After the mixture was stirred one hour at room temperature, 5.6 g (0.04 mole) of methyl iodide was added dropwise. The mixture was stirred at room temperature overnight, then poured into water and extracted with ether. The ether extracts were backwashed with water three times, then dried and concentrated. The crude solid was recrystallized from hexane to give 4.3 g of product, m.p. 129°–129.5°.

Anal. Calcd. for $C_{17}H_{13}F_2N$: C, 75.82; H, 4.87; N, 5.20. Found: C, 75.89, 75.78; H, 4.98, 4.97; N, 5.18, 5.10.

Other 2,3-diarylpyrroles prepared by these procedures are given in Table I.

TABLE I 2,3-Diarylpyrroles

| Preparation | $R_2$ | $R_3$ | $R_1$ | m.p. °C. |
|---|---|---|---|---|
| 6 | 4-ClC$_6$H$_4$ | 4-ClC$_6$H$_4$ | H | 124–127 |
| 7 | 4-FC$_6$H$_4$ | 4-FC$_6$H$_4$ | H | 119.5–120.5 |
| 8 | C$_6$H$_5$ | 3,4-diClC$_6$H$_3$ | H | 112–113 |
| 9 | 4-FC$_6$H$_4$ | 4-BrC$_6$H$_4$ | H | 129–130 |
| 10 | C$_6$H$_5$ | 3-pyridyl | H | 190–192 |
| 11 | 4-CH$_3$OC$_6$H$_4$ | 4-CH$_3$OC$_6$H$_4$ | H | oil |
| 12 | 4-CH$_3$C$_6$H$_4$ | 4-CH$_3$C$_6$H$_4$ | H | 128–129 |
| 13 | 4-FC$_6$H$_4$ | 4-(CH$_3$)$_2$NC$_6$H$_4$ | H | 200–201 |
| 14 | 4-FC$_6$H$_4$ | 3-pyridyl | H | 173–174 |
| 15 | 4-FC$_6$H$_4$ | 4-CH$_3$SC$_6$H$_4$ | H | 164–165 |
| 16 | 4-FC$_6$H$_4$ | 4-CH$_3$—SO$_2$C$_6$H$_4$ | H | 268–270 |

EXAMPLE 1

4,5-Bis(4-fluorophenyl)-α,α-bis(trifluoromethyl)-1H-pyrrole-2-methanethiol

Into a solution of 2.6 g (0.01 mole) of 2,3-bis(4-fluorophenyl)-1H-pyrrole in 100 ml toluene was distilled 2.0 g (0.011 mole) of hexafluorothioacetone, prepared by pyrolysis of the dimer according to the method of W. J. Middleton et al., *J. Org. Chem.*, 30, 1375 (1965). The mixture was stirred at room temperature approximately one-half hour, then was concentrated by rotary evaporation. The residue was purified by chromatography on silica gel, eluting with hexane/toluene (80/20). The chromatographed product was recrystallized from hexane to give 1.0 g of product, m.p. 114°–115°.

Anal. Calcd. for $C_{19}H_{11}F_8NS$: C, 52.18; H, 2.54; N, 3.20. Found: C, 52.00; H, 2.71; 52.01; H, 2.72. N, 3.08. N, 3.06.

Other 4,5-diaryl-α,α-bis(polyfluoromethyl)-1H-pyrrole-2-methanethiols that can be prepared by a similar procedure are given in Table II.

TABLE II

| Ex. | $R_1$ | $R_2$ | $R_3$ | $R_4$ | $R_5$ | $R_6$ | $R_7$ | m.p.°(C.) |
|---|---|---|---|---|---|---|---|---|
| 2 | H | 4-FC$_6$H$_4$ | 4-FC$_6$H$_4$ | CF$_3$ | CF$_3$ | CH$_3$ | H | |
| 3 | H | 4-CH$_3$OC$_6$H$_4$ | 4-CH$_3$OC$_6$H$_4$ | CF$_3$ | CF$_3$ | H | H | |
| 4 | H | 4-FC$_6$H$_4$ | 4-FC$_6$H$_4$ | CF$_3$ | CF$_3$ | H | CH$_3$ | |
| 5 | H | 4-FC$_6$H$_4$ | 4-BrC$_6$H$_4$ | CF$_3$ | CF$_3$ | H | H | |
| 6 | H | 4-CH$_3$C$_6$H$_4$ | 4-CH$_3$C$_6$H$_4$ | CF$_3$ | CF$_3$ | H | H | |
| 7 | CH$_3$ | 4-FC$_6$H$_4$ | 4-FC$_6$H$_4$ | CF$_3$ | CF$_3$ | H | H | |
| 8 | H | 4-FC$_6$H$_4$ | 4(CH$_3$)$_2$NC$_6$H$_4$ | CF$_3$ | CF$_3$ | H | H | |
| 9 | H | 4-ClC$_6$H$_4$ | 4-ClC$_6$H$_4$ | CF$_3$ | CF$_3$ | H | H | |
| 10 | H | C$_6$H$_5$ | C$_6$H$_5$ | CF$_3$ | CF$_3$ | H | H | |
| 11 | H | 4-FC$_6$H$_4$ | 4-FC$_6$H$_4$ | CF$_2$Cl | CF$_2$Cl | H | H | |
| 12 | H | 4-FC$_6$H$_4$ | 4-FC$_6$H$_4$ | CF$_2$H | CF$_3$ | H | H | |
| 13 | —CH$_2$CH$_3$ | 4-FC$_6$H$_4$ | 4-FC$_6$H$_4$ | CF$_3$ | CF$_3$ | H | H | |
| 14 | H | 4-FC$_6$H$_4$ | 4-FC$_6$H$_4$ | CF$_3$ | CF$_3$ | —CH$_2$CH$_2$CH$_3$ | H | |
| 15 | H | 4-FC$_6$H$_4$ | 4-FC$_6$H$_4$ | CF$_3$ | CF$_3$ | H | C$_6$H$_{13}$— | |
| 16 | H | 3-F, 4-ClC$_6$H$_3$ | 4-CH$_3$OC$_6$H$_4$ | CF$_3$ | CF$_3$ | H | H | |
| 17 | CH$_3$ | 4-FC$_6$H$_4$ | 4-FC$_6$H$_4$ | CF$_3$ | CF$_3$ | CH$_3$ | CH$_3$ | |
| 18 | H | 4-FC$_6$H$_4$ | 3-pyridyl | CF$_3$ | CF$_3$ | H | H | |
| 19 | H | 4-FC$_6$H$_4$ | 4-CH$_3$SO$_2$C$_6$H$_4$ | CF$_3$ | CF$_3$ | H | H | |
| 20 | H | 4-FC$_6$H$_4$ | 4-FC$_6$H$_4$ | CFCl$_2$ | CF$_2$Cl | H | H | |
| 21 | H | 4-FC$_6$H$_4$ | 4-FC$_6$H$_4$ | CF$_3$ | CF$_3$ | 4-NO$_2$C$_6$H$_4$CH$_2$— | H | |
| 22 | H | 4-FC$_6$H$_4$ | 4-FC$_6$H$_4$ | CF$_3$ | CF$_3$ | H | -CH$_2$C$_6$H$_5$ | |

TABLE II-continued $$\begin{array}{c} R_2 \diagdown \diagup R_1 \\ \diagup\phantom{xx}\diagdown R_4 \\ R_3 \diagdown \phantom{x} N \phantom{x} \diagup C-SR_7 \\ \phantom{xxx} | \phantom{xxx} | \\ \phantom{xxx} R_6 \phantom{x} R_5 \end{array}$$

| Ex. | $R_1$ | $R_2$ | $R_3$ | $R_4$ | $R_5$ | $R_6$ | $R_7$ | m.p.°(C.) |
|---|---|---|---|---|---|---|---|---|
| 23 | H | 4-FC$_6$H$_4$ | 4-FC$_6$H$_4$ | CF$_3$ | CF$_3$ | H | $\underset{\underset{O}{\|}}{CCH_3}$ | |
| 24 | H | 4-FC$_6$H$_4$ | 4-FC$_6$H$_4$ | CF$_3$ | CF$_3$ | $\underset{\underset{O}{\|}}{CCH_3}$ | H | |

DOSAGE FORMS

The antiarthritic agents of this invention can be administered to treat arthritis by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.01 to 40 milligrams per kilogram of body weight. Ordinarily 0.05 to 20, and preferably 0.1 to 4 milligrams per kilogram per day given in divided doses 2 to 4 times a day or in sustained release form is effective to obtain desired results.

Dosage forms (compositions) suitable for internal administration contain from about 1.0 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coating for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propylparaben and chlorobutanol.

Suitable pharmaceutical carriers are described in *Remington's Pharmaceutical Sciences*, E. W. Martin, a standard reference text in this field.

Useful pharmaceutical dosage forms for administration of the compounds of this invention can be illustrated as follows:

Capsules

A large number of unit capsules are prepared by filling standard two-piece hard gelatin capsules each with 50 milligrams of powdered active ingredient 175 milligrams of lactose, 24 milligrams of talc, and 6 milligrams magnesium stearate.

A mixture of active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by filtration.

Suspension

An aqueous suspension is prepared for oral administration so that each 5 milliliters contain 10 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Injectable

A parenteral composition suitable for administration by injection is prepared by stirring 1% by weight of active ingredient in sodium chloride injection U.S.P. XV and sterilizing by filtration.

Use

To detect and compare the anti-inflammatory activities of compounds in this series and standard drugs, a test was used based on a standard model of arthritis for which there is good correlation with human efficacy. The model is adjuvant-induced arthritis in rats. Federation Proceedings, Vol. 32, No. 2, 1973, "Models Used for the Study and Therapy of Rheumatoid Arthritis'—Symposium of the American Society for Pharmacology and Experimental Therapeutics—states "The rat polyarthritis produced by intradermal injection of a suspension of *Mycobacterium tuberculosis* is mineral oil (adjuvant) has been used extensively for the screening of drugs of potential use in rheumatoid arthritis."

Compounds of this invention have shown activity in adjuvant-induced arthritis in rats which is widely recognized as a good model of human rheumatoid arthritis.

METHODS

Established Adjuvant-Induced Arthritis in Rats

Lewis (Wistar) male rats (Charles River Breeding Laboratories, Wilmington, Mass.) weighing 175-200 grams were injected subcutaneously with 0.1 ml of adjuvant in the plantar area of the right hind paw. The adjuvant was prepared by bead-milling, heat-killed, lyophilized *Mycobacterium butyricum* (Difco #0640) in light mineral oil (Fisher Scientific Co. #0-119 Paraffin Oil-Saybolt Viscosity 125/135) 5 mg/ml. Twenty non-arthritic control rats were injected with mineral oil. The animals received water and Wayne Lab-Blox ad libitum*.

*while on a 10-hour light—14 hour-dark cycle

The rats were held for 14 days to allow the development of polyarthritis. The volume of the uninjected, left-hind paw of each rat was measured by using a Ugo Basile Volume Differential Meter, Model 7101. Adjuvant injected rats showing no evidence of arthritis were discarded and the arthritic rats were distributed into groups of 10 having equal mean paw volumes with equal standard deviation. Non-arthritic (oil-injected) control rats were distributed to 2 groups of 10. Suspensions of test compounds were prepared for dosing by bead-milling (4 mm glass beads in rubber stoppered serum bottles) for 4-5 hours in aqueous 1% polyvinyl alcohol, 5% gum acacia and 0.5% methylparaben.

Test compounds were given orally by gavage once daily for 7 days (days 14-20). The 2 groups of oil injected, non-arthritic control rats and the 2 groups of arthritic control rats received vehicle only for 7 days. Paw volumes (uninjected left hind paw) were measured 20 hours after the last dose (on day 21).

Percent decrease from control mean paw volume was calculated with the following formula:

$$\frac{\text{Arthritic Vehicle Control Mean Paw Volume (ml)} - \text{Arthritic Treatment Mean Paw Volume (ml)}}{\text{Arthritic Vehicle Control Mean Paw Volume (ml)} - \text{Non-Arthritic Vehicle Control Mean Paw Volume (ml)}} \times 100 =$$

% Decrease from Control Mean Paw Volume

Dose-response regression lines of the % decrease were plotted on semi-log paper and the $ED_{50}\%$ for decrease from control paw volume was estimated by inspection.

RESULTS

TABLE III

Antiarthritic Activity

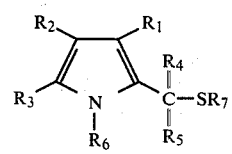

| Ex. | $R_1$ | $R_2$ | $R_3$ | $R_4$ | $R_5$ | $R_6$ | $R_7$ | Adjuvant Arthritis ED (mg/kg) |
|---|---|---|---|---|---|---|---|---|
| 1 | H | 4-$FC_6H_4$ | 4-$FC_6H_4$ | $CF_3$ | $CF_3$ | H | H | 1.0 |

What is claimed is:

1. A compound of the formula

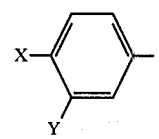

wherein
$R_1$=H or $C_1$-$C_2$ alkyl;
$R_2$ and $R_3$ independently=3-pyridyl or

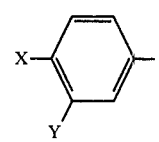

where
X=H, F, Cl, Br, $C_1$-$C_2$ alkyl, $C_1$-$C_2$ alkoxy, di($C_1$-$C_2$ alkyl)amino or $CH_3S(O)_n$—where n=0, 1 or 2; and
Y=H, F or Cl;
with the proviso that when Y is F or Cl, then X is F or Cl;
$R_4$ and $R_5$ independently=$CF_3$, $CF_2H$, $CF_2Cl$, or $CFCl_2$;
$R_6$ and $R_7$ independently=H, $C_1$-$C_6$ alkyl, $C_1$-$C_6$ alkanoyl, benzyl or benzyl substituted with up to two atoms selected from the group consisting of F, Cl, Br, $NO_2$, and $CF_3$; or
a pharmaceutically suitable acid addition salt where $R_2$ or $R_3$ is 3-pyridyl or dialkylaminophenyl; or
a pharmaceutically suitable metal salt where $R_7$ is H.

2. A compound of claim 1 where $R_1$=H or $CH_3$.

3. A compound of claim 1 where $R_2$ and $R_3$ independently= and where X=Cl, F or $CH_3O$ and Y=H.

4. A compound of claim 1 wherein $R_4$ and $R_5$ are both $CF_3$.

5. A compound of claim 1 wherein $R_6 = H$ or $CH_3$.

6. A compound of claim 1 wherein $R_7 = H$ or $CH_3$.

7. A compound of claim 1 wherein $R_1 = H$ or $CH_3$; $R_2$ and $R_3$ independently =

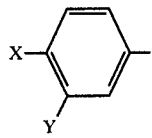

where $X = Cl$, F or methoxy and $Y = H$; and $R_4$ and $R_5$ are both $CF_3$; $R_6 = H$ or $CH_3$; and $R_7 = H$ or $CH_3$.

8. The compound of claim 1 which is 4,5-bis(4-fluorophenyl)-α,α-bis(trifluoromethyl)-1H-pyrrole-2-methanethiol.

9. A pharmaceutical composition consisting essentially of a suitable pharmaceutical carrier and an effective antiinflammatory amount of a compound of claim 1.

10. A pharmaceutical composition consisting essentially of a suitable pharmaceutical carrier and an effective antiinflammatory amount of a compound of claim 2.

11. A pharmaceutical composition consisting essentially of a suitable pharmaceutical carrier and an effective antiinflammatory amount of a compound of claim 3.

12. A pharmaceutical composition consisting essentially of a suitable pharmaceutical carrier and an effective antiinflammatory amount of a compound of claim 4.

13. A pharmaceutical composition consisting essentially of a suitable pharmaceutical carrier and an effective antiinflammatory amount of a compound of claim 5.

14. A pharmaceutical composition consisting essentially of a suitable pharmaceutical carrier and an effective antiinflammatory amount of a compound of claim 6.

15. A pharmaceutical composition consisting essentially of a suitable pharmaceutical carrier and an effective antiinflammatory amount of a compound of claim 7.

16. A pharmaceutical composition consisting essentially of a suitable pharmaceutical carrier and an effective antiinflammatory amount of the compound of claim 8.

17. A method of treating arthritis in a mammal which comprises administering to the mammal an antiarthritic amount of a compound of claim 1.

18. A method of treating arthritis in a mammal which comprises administering to the mammal an antiarthritic amount of a compound of claim 2.

19. A method of treating arthritis in a mammal which comprises administering to the mammal an antiarthritic amount of a compound of claim 3.

20. A method of treating arthritis in a mammal which comprises administering to the mammal an antiarthritic amount of a compound of claim 4.

21. A method of treating arthritis in a mammal which comprises administering to the mammal an antiarthritic amount of a compound of claim 5.

22. A method of treating arthritis in a mammal which comprises administering to the mammal an antiarthritic amount of a compound of claim 6.

23. A method of treating arthritis in a mammal which comprises administering to the mammal an antiarthritic amount of a compound of claim 7.

24. A method of treating arthritis in a mammal which comprises administering to the mammal an antiarthritic amount of the compound of claim 8.

* * * * *